US007996272B2

(12) United States Patent  (10) Patent No.: US 7,996,272 B2
Smith et al.  (45) Date of Patent: Aug. 9, 2011

(54) METHOD AND SYSTEM FOR ORDERING STENT GRAFTS

(75) Inventors: Allan Joseph Hilling Smith, Queensland (AU); David Andrew Coulson, Queensland (AU)

(73) Assignees: William A. Cook Australia Pty. Ltd., Queensland (AU); Cook Medical Technologies LLC, Bloomington, IN (US)

( * ) Notice: Subject to any disclaimer, the term of this patent is extended or adjusted under 35 U.S.C. 154(b) by 825 days.

(21) Appl. No.: 11/546,775

(22) Filed: Oct. 12, 2006

(65) Prior Publication Data

US 2007/0112581 A1 May 17, 2007

Related U.S. Application Data

(60) Provisional application No. 60/725,730, filed on Oct. 12, 2005.

(51) Int. Cl.
 *G06Q 30/00* (2006.01)
(52) U.S. Cl. ..................................... 705/26.1
(58) Field of Classification Search ............ 705/26, 705/27
 See application file for complete search history.

(56) References Cited

U.S. PATENT DOCUMENTS

| 2002/0052807 A1 | 5/2002 | Han et al. | |
| 2003/0018404 A1* | 1/2003 | Hruby | 700/97 |
| 2003/0200120 A1* | 10/2003 | Binkert | 705/3 |

FOREIGN PATENT DOCUMENTS

JP 2001/079097 A 3/2001
WO PCT/US2006/39848 10/2007

OTHER PUBLICATIONS

Hyodoh, H., Katagiri, Y., Sakai, T., Hyodoh, K., Akiba, H., & Hareyama, M.. (2005). Creation of individual ideally shaped stents using multi-slice CT: in vitro results from the semi-automatic virtual stent (SAVS) designer. European Radiology, 15(8), 1623-1628. Retrieved Mar. 22, 2011, from ProQuest Health and Medical Complete.*
ISR/PCT/US2006/39848, Oct. 25, 2007, EPO.

* cited by examiner

*Primary Examiner* — Jeffrey A Smith
*Assistant Examiner* — Courtney Stopp
(74) *Attorney, Agent, or Firm* — Richard J. Godlewski

(57) ABSTRACT

A system for designing and ordering a stent graft is described. The system includes a user interface for designing and ordering the stent graft, and a centralised data processor remote from and in communication with the user interface for processing and storing entered information. The user interface further includes a selection portion for selecting a stent graft design and a design portion for entering a plurality of design parameters related to the stent graft design. A verification portion is also provided to verify details of a completed stent graft design with an ordering portion to order the completed stent graft design. In one embodiment the verification portion includes the capability to display a 3-dimensional view of the completed stent graft design.

15 Claims, 17 Drawing Sheets

*Figure 10*
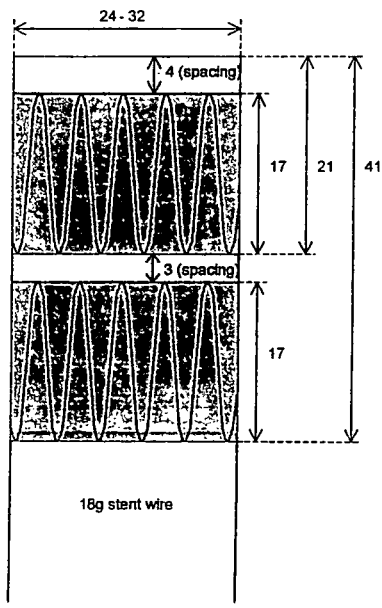
*Figure 11a*
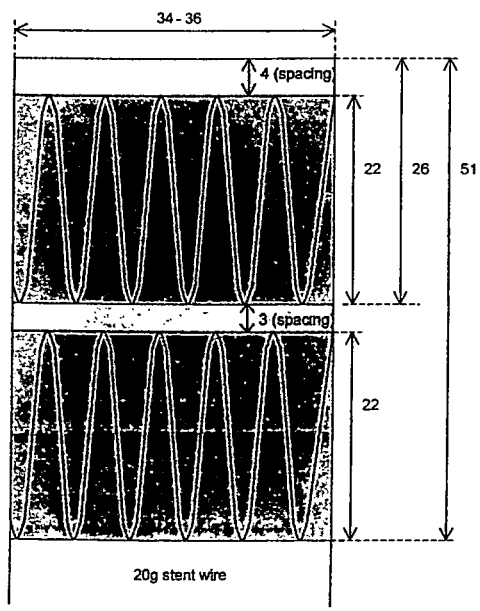
*Figure 11b*

METHOD AND SYSTEM FOR ORDERING STENT GRAFTS

CROSS-REFERENCE TO RELATED APPLICATIONS

This application claims priority of provisional application Ser. No. 60/725,730, filed Oct. 12, 2005.

TECHNICAL FIELD

The present invention relates to a system for ordering medical implants. In a particular form the present invention relates to a system for designing, specifying and ordering a graft for insertion by a surgeon into a patient.

BACKGROUND OF THE INVENTION

The use of surgically implanted grafts has greatly improved the quality of life of patients suffering vascular and other related diseases. As these are highly specialised medical devices which are customised to a high degree according to the type of graft and the patient being treated, sophisticated design and ordering methodologies have been developed to ensure that physicians are able to reliably design or specify the required graft and then order the graft in a timely and cost effective manner.

One such ordering system involves the use of specialised software which is distributed to physicians. This software leads the physician through the graft design process and validates design parameters as entered by the physician. As an example, the software would display the particular design parameter such as the diameter of a renal aorta, then provide a recommended value for this diameter and further limit the range of diameters that a physician may enter when designing or specifying this aspect of the graft. In this example of graft design, a number of standardised design parameters and associated locations have been developed to specify a given type of graft.

Once the physician has completed the graft design, an order suitable for sending to the manufacturer of the graft can be printed from the ordering system. This order can include all relevant information such as patient and physician details, graft design specification and a purchase order number.

Alternatively the physician may send the order, including the specified graft information to a hospital, where the operation is to be performed and instruct the hospital to raise a purchase order number. This number is then forwarded with the order to the manufacturer of the graft. Whilst this system is clearly preferable to a purely paper based system that does not include any intrinsic validation of the graft design as part of the order generation process, this approach suffers from a number of serious disadvantages.

One of these disadvantages is that some physicians will continue to use older versions of the software instead of the latest version. As new and improved products are developed, the software will require updating to include these additional products. This then requires the physical distribution of software updates to each physician who wishes to use the software. This adds greatly to the time and costs involved in maintaining the software. As a consequence, individual physicians may be using many different versions of software which can cause confusion in the ordering process with the manufacturer having to be familiar with a number of different types of ordering schemes corresponding to different software versions.

Typically, the centralised office that receives a physician's order is then responsible for the coordinating and shipping of the complete order. The order may be met either by using standard sized components from existing stock, manufacturing customised components or otherwise by ordering customised components that are not manufactured locally from another site that manufactures the required component. Given the degree of complexity in this process, it is critical that an ordering system provide the relevant office with a uniform and efficient format to allow them to coordinate this process.

Another significant disadvantage arising from relying on software installed on individual machines, is that the relevant software must be installed on a computer that the physician has access to. This installation process will often require phone support by the manufacturer, especially if the software is being installed by someone without information technology skills. This further adds to the cost of supporting the software and also to the degree of inconvenience that a user of the software will suffer each time a new version of the software requires installation. As a consequence, manufacturers have had to consider carefully whether to release a new software version having improved design and verification procedures related to more complicated graft designs. As these features are complex to integrate into the software design process it is likely that a number of versions will have to be released in a relatively short time with all of the associated difficulties described above.

It is an object of the present invention to provide a system for designing and ordering a medical implant capable of being readily updated.

It is a further object of the present invention to provide a system for designing and ordering a medical implant capable of processing design and ordering information in a centralised location.

SUMMARY OF THE INVENTION

In a first aspect the present invention provides a system for designing and ordering a stent graft, the system comprising:
 a user interface for designing and ordering the stent graft, the user interface further comprising;
 a selection portion for selecting a stent graft design;
 a design portion for entering a plurality of design parameters related to the stent graft design;
 a verification portion to verify details of a completed stent graft design; and
 an ordering portion to order the completed stent graft design;
 and a centralised data processor remote from and in communication with the user interface for processing and storing information entered into the user interface.

By having the user interface located remotely to the centralised data processor and furthermore being served by the centralised data processor, the user interface may be located in a doctor's office or a hospital. As the user interface originates from the centralised data processor there is no requirement to update any software at each of the remote locations when either the functionality or the user interface of the designing and ordering system is updated. Furthermore all of the design and ordering information will be processed by the centralised data processor at the centralised location.

Preferably, the verification portion includes a design verification screen to display a view of the completed stent graft design.

Preferably, the view is a 3-dimensional view of the completed stent graft design.

Preferably, the 3-dimensional view is reorientable to inspect the completed stent graft design.

Preferably, the 3-dimensional view is zoomable to inspect the completed stent graft design.

Preferably, the 3-dimensional view is overlaid with a 3-dimensional view of a patient stent graft site for the completed stent graft design.

Preferably, the selection portion includes a selection of a stent graft having at least one fenestration.

Preferably, the design portion includes at least one screen, the at least one screen adapted to capture fenestration design information related to the at least one fenestration.

Preferably, the fenestration design information includes the fenestration type.

Preferably, the fenestration type is selectable from a large, small or scallop type fenestration.

Preferably, the fenestration design information includes the location of the at least one fenestration.

Preferably, the location of the at least one fenestration includes a distance from an edge of the stent graft.

Preferably, the location of the least one fenestration is selectable as a clock position.

Preferably, the fenestration design information includes the size of the at least one fenestration.

Preferably, the system includes a validation capability to validate the fenestration design information related to the at least one fenestration.

Preferably, the validation capability includes validating a size, location and type of the at least one fenestration.

Preferably, the validation capability, includes in the case of more than one fenestration, validating the combination of fenestrations for the stent graft design.

Preferably, the system includes the storage and recall of an incomplete stent graft design.

In a second aspect the present invention accordingly provides a system for designing and ordering a stent graft including at least one fenestration, the system comprising:

a user interface for designing and ordering the stent graft, the user interface further comprising;

a selection portion for selecting a stent graft design;

a design portion for entering a plurality of design parameters related to the stent graft design;

a verification portion to verify details of a completed stent graft design, the verification portion including a 3-dimensional view of the completed stent graft design; and an ordering portion to order the completed stent graft design; and a centralised data processor remote from and in communication with the user interface for processing and storing information entered into the user interface.

In a third aspect the present method accordingly provides a method for the design and ordering of a stent graft, the method including the steps:

designing or specifying a value for a physical parameter of a stent graft design employing a user interface;

validating the value against predetermined criteria related to the physical parameter;

storing the value in a centralised location remote from the user interface;

verifying the stent graft design on completion of the design of the stent graft; and ordering the stent graft.

BRIEF DESCRIPTION OF THE DRAWING

A preferred embodiment of the present invention will be discussed with reference to the accompanying drawings wherein:

FIG. 10 is a depiction of the fenestration design and specification screen;

FIG. 11a is a schematic view of the physical dimensions of the proximal body of a graft for 18 g stent wire;

FIG. 11b is a schematic view of the physical dimensions of the proximal body of a graft for 20 g stent wire;

DETAILED DESCRIPTION

Figure 1:
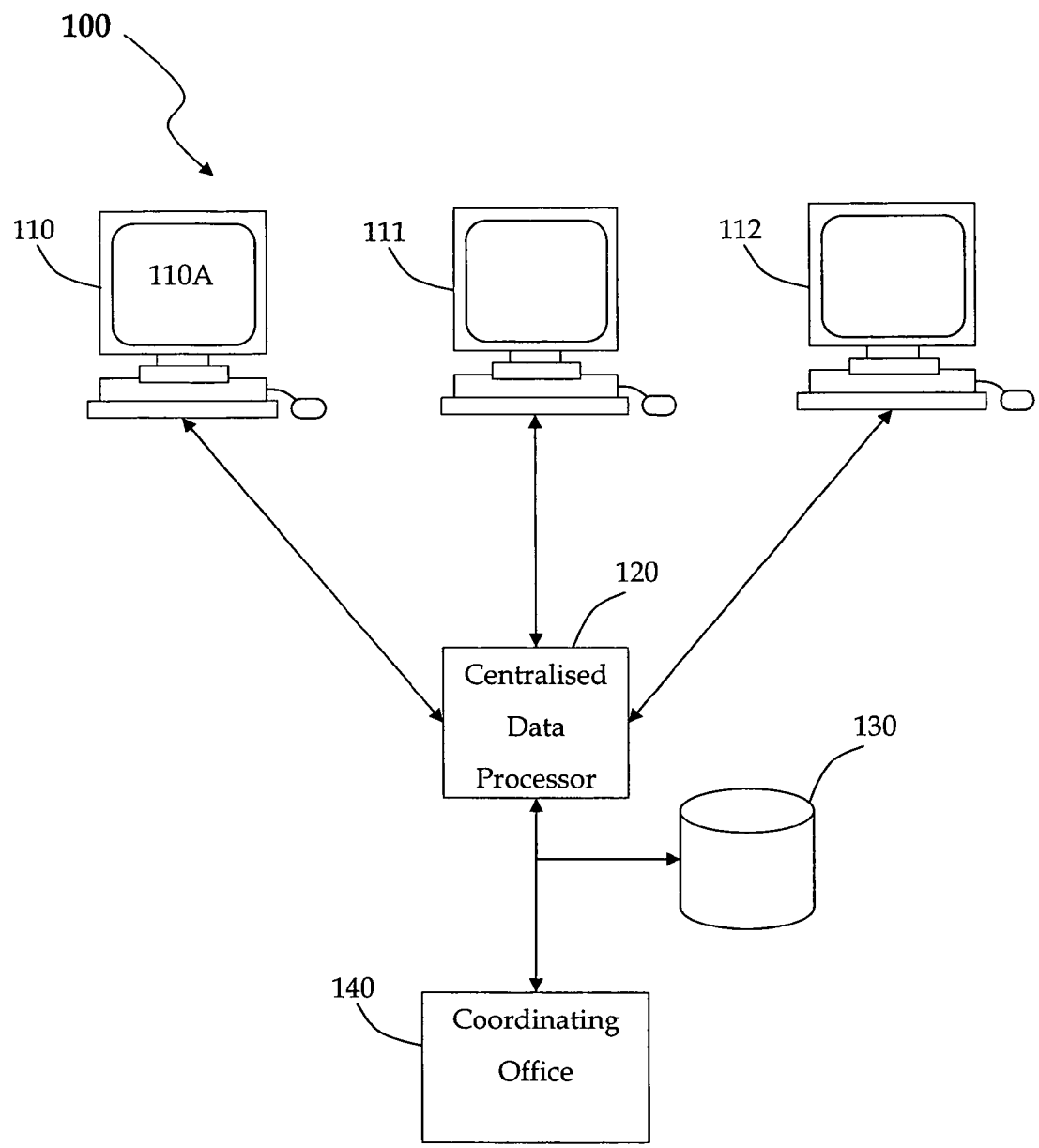
FIG. 1 is a general overview of the system components included in a system for designing and ordering a stent graft according to apreferred embodiment of the present invention.

Referring now to FIG. 1, there is shown an overview of design and ordering system 100 for designing and ordering a stent graft according to a preferred embodiment. Throughout the description the invention is described by way of reference to the design and ordering of graft implants which may or may not be fenestrated according to the ultimate location of the graft within the patient. As would be apparent to those skilled in the art, the present invention should not be limited to this application but may be equally applied to other types of medical implants which require a high degree of customisation within a set of predetermined parameters.

Design and ordering system 100 includes a centralised data processor 120 including database 130 that provides detailed ordering and design information to manufacturing coordination infrastructure 140 by suitable network connection or the like. Internet based ordering stations 110, 111, 112 access centralised data processor 120 via the World Wide Web (WWW) and as such may be any suitable data processing device capable of implementing a web browser thereby providing user interface 110A. To allow for Internet based access, centralised data processor 120 is implemented as a web application running on a web server. In this preferred embodiment Apache web server software is used and centralised data processor 120 includes standard server protection facilities such as a de-militarised zone, firewall and antivirus capabilities.

To provide for secure transmission of user data on specified web pages, all network traffic is encrypted using Hyper Text Transfer Protocol Secure Socket (HTTPS) protocol which is configured as an option within the web server. Centralised data processor 120 capability is implemented in JAVA™ utilising Java Servlets and Enterprise Java Beans (EJB). EJB allows for system scalability, to meet user demands of approximately 500 plus potential system users.

As the web user interface 110A for software applications involves a stateless HTTP request/response model it is essential to ensure that critical information related to the graft design and ordering process is being captured and validated correctly. In this preferred embodiment, data entry required to design a graft has been separated into a series of linked web pages. The data captured on an individual page is retained during an individual user session (on centralised dataprocessor 120) so that it can be combined into a completed graft design at the end of the data entry process.

On each web page, specific validation is completed to ensure that data is entered correctly before it is transmitted to centralised data processor 120. When cross validation of data entered across two or web more pages isrequired, this is performed after all the data has been transmitted to centralised data processor 120. Another alternative is to perform this cross validation on the client side. However, this would require data captured from one screen to be sent back as "hidden" data on the display of the next web page so that it is available for client side validation after related data has been filled in on the second web page by a user.

Accordingly, in this preferred embodiment data is only validated for the current web page on the client side, and all cross page validation is performed on centralised data processor 120. Client side validation therefore includes checking data types and formats (e.g. checking that only numbers have been entered into numeric fields, valid dates have been entered in date fields or that the correct email address format has been employed), range checking (e.g. that the "From date" is less than or equal to "To date"), mandatory field checking, and minimum/maximum field length.

If validation performed on centralised data processor 120 identifies any errors, the associated web page generating the errors will be redisplayed indicating the appropriate error message(s) requiring correction before the user can proceed to the next web page in the graft design and ordering process.

As would be appreciated by those skilled in the art, whilst the JAVA™ development environment provides a convenient development platform for the present invention, other client server based methodologies are also contemplated to be within the scope of the invention. Database 130 associated with centralised data processor 120 is implemented using a Structured Query Language (SQL) database as is known in the art.

Figure 2:
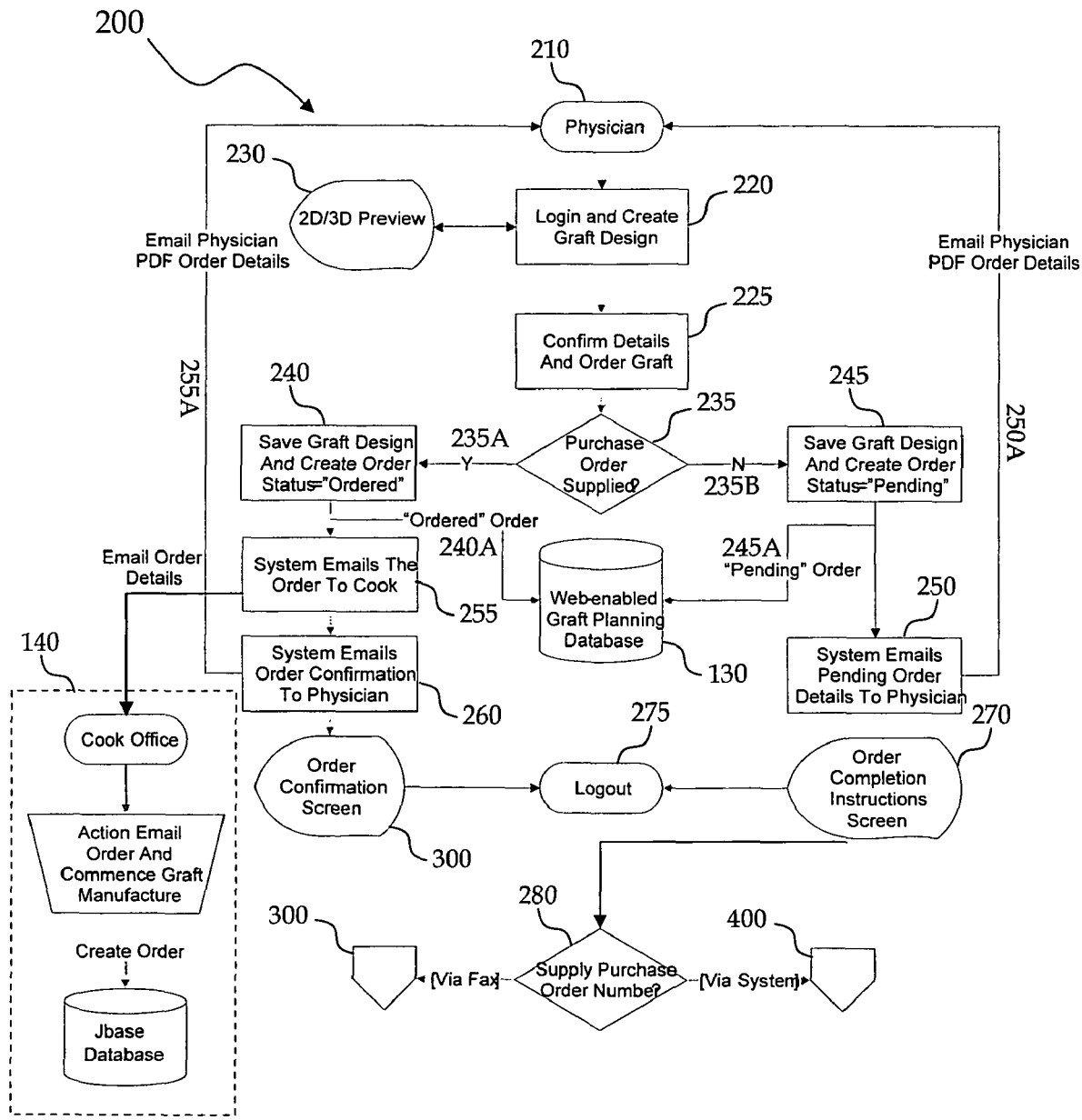
FIG. 2 is a system flowchart of the design and ordering system for a stent graft according to apreferred embodiment of the present invention.

Referring now to FIG. 2, there is shown a flowchart 200 depicting an preferred embodiment of the present invention. Physician 210 first logs onto design and ordering system 100 and creates graft design 220. As part of the design process physician 210 is able to inspect a 3D preview of the graft design. Once the design is completed to the physician's satisfaction the details are confirmed and the graft ordered 225.

The next step is to determine whether a purchase order has been supplied 235. In the event of a purchase order being supplied 235A by the physician 210 the ordering system saves the graft design and corresponding order and gives the order the status of ORDERED 240. The status of the order is then further saved 240A in central database 130. Design and ordering system 100 emails 255 the order details to manufacturing coordination site 140 which in this embodiment is a Cook Office which typically liaises with the relevant manufacturing facility. In logs in 405 to design and ordering system 100 and selects the relevant order from order summary screen 410 and displays the order detail 415 whereupon the purchase order number is entered 420 and the order with these new details are saved 420. Once again the order status is updated to ORDERED and design and ordering system 100 emails the completed order to manufacturing coordination 140 in a similar manner to that depicted in FIG. 1.

As all order details are stored in central database 130 and furthermore as the order details and related data are processed at centralised data processor 120 this allows the physician to access their current or pending order details, begin a new graft order or alternatively delete a graft order by simply logging into the centralised data processor 120 by its front end web page which functions as user interface 110A.

The present invention offers a number of significant advantages by way of the graft design and verification procedure employed. As outlined in FIG. 2 the physician will create a graft design 220 and then verify this design by inspecting 230 both 2D and 3D representations of the final design. This process will now be described in more detail.

Figure 5:
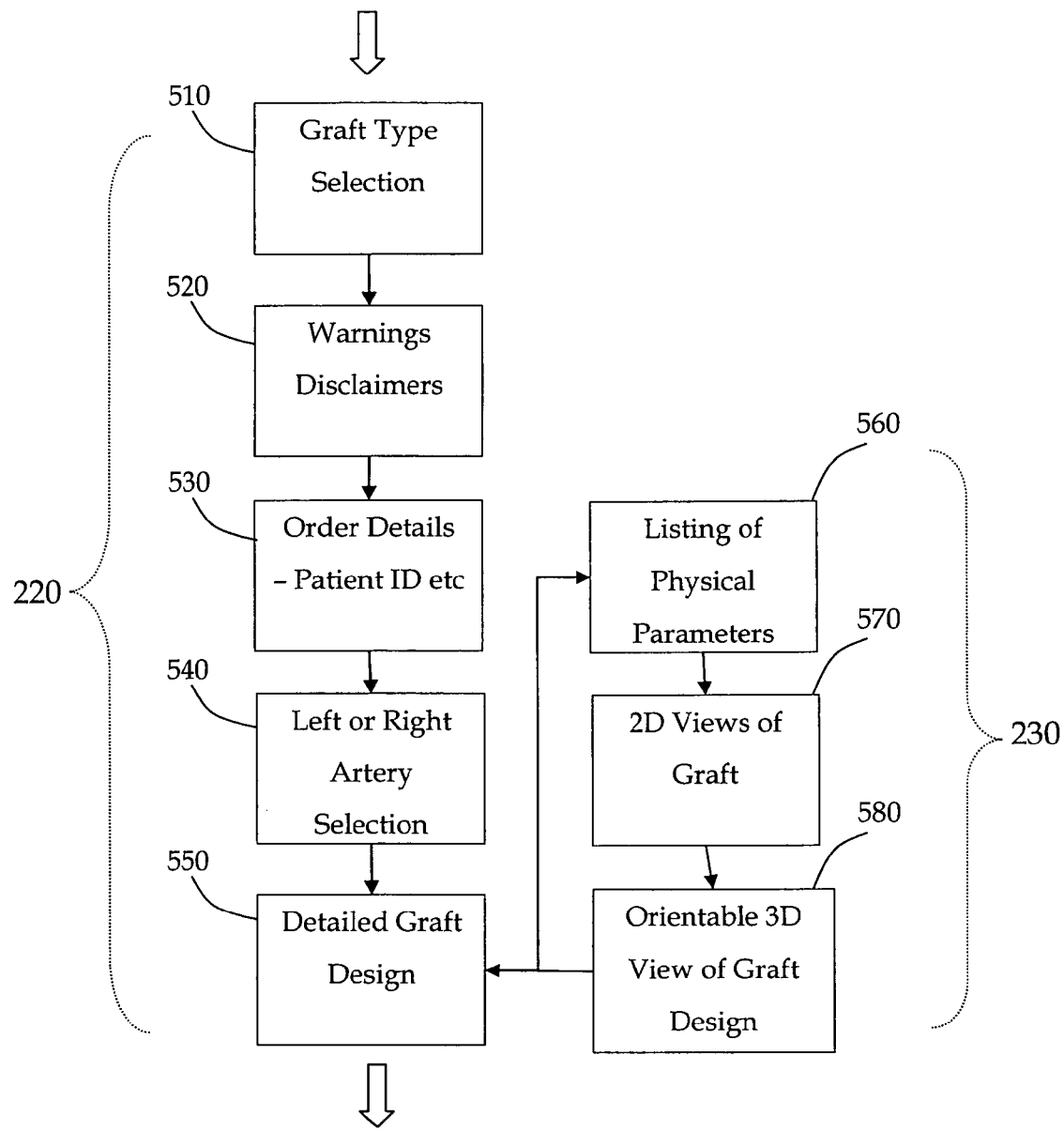
FIG. 5 is a system flowchart overview of the steps involved in the design and verification of a graft including fenestrations according to a preferred embodiment of the present invention.
Figure 6:
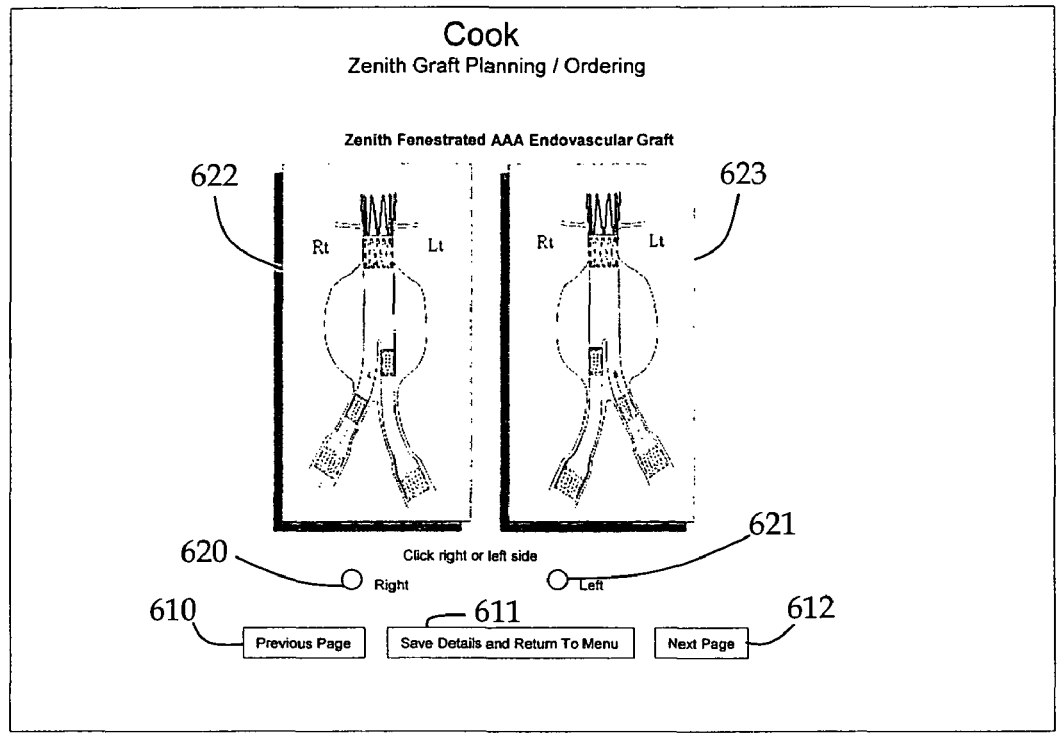
FIG. 6 is a depiction of the graft orientation selection screen.

Referring now to FIG. 5, there is shown an overview flowchart of the selection, design, ordering and verification process for a new graft. A graft design is first selected via a selection portion 510 of user interface 110A. In this preferred embodiment the present invention is described by reference to the selection, design and ordering (as indicated generally by 220) and verification (as indicated generally by 230) of a Zenith Fenestrated AAA Endovascular Graft. Once the graft design has been selected, a series of warnings and disclaimers are displayed 520 according to the type of graft selected. This provides a number of reminders to the physician of issues that must be taken into account in the design process. Details such as the patient identification details, physician and ordering details are then entered in the ordering portion 530 of user interface 110A. The next step (see also FIG. 6) is the selection of either a right or left side endovascular graft 540 and then the detailed design of the graft commences in the design portion 550 of user interface.

Once the detailed design has been initially completed, the physician is then able to review the design in verification portion 230 of user interface 110A. This involves first inspecting a listing of the relevant design parameters 560 of the designed graft (see also FIGS. 22 and 23). This is followed by inspection of 2D views of the graft 570 (see also FIG. 24) and finally a 3D orientable and zoomable view 580 of the graft design (see also FIG. 25) may be reviewed providing the physician with the capability to review the design from all angles to ensure it matches with the design requirements. This detaile ddesign and verification process will now be described in detail.

Figure 7:
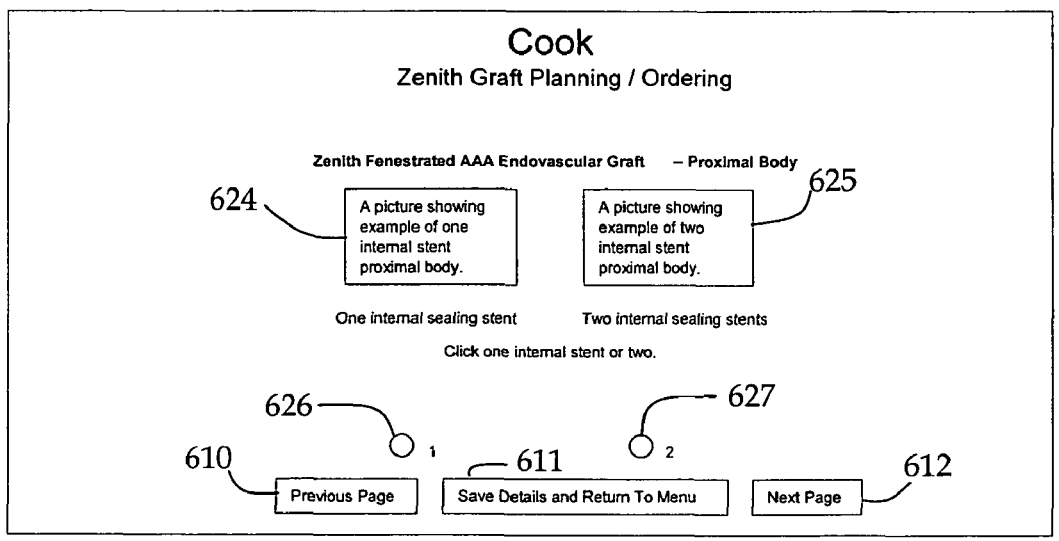
FIG. 7 is a depiction of the proximal body number of stents selection screen for the graft.

Referring now to FIG. 7, in the first stage of the detailed design process the physician is given the option of selecting a graft with either one 626 or two 627 internal sealing stents for the proximal end of the proximal body. Example images showing the proximal body of a one internal sealing stent 624 or two internal sealing stent 625 are displayed to aid the physician when making a selection. During the design process the physician may select to go to the previous page or screen 610 or alternatively save the current design at this stage and return 611 to the top level menu. Typically, once this step has been completed the physician will select to go to the next page 612.

Figure 8:
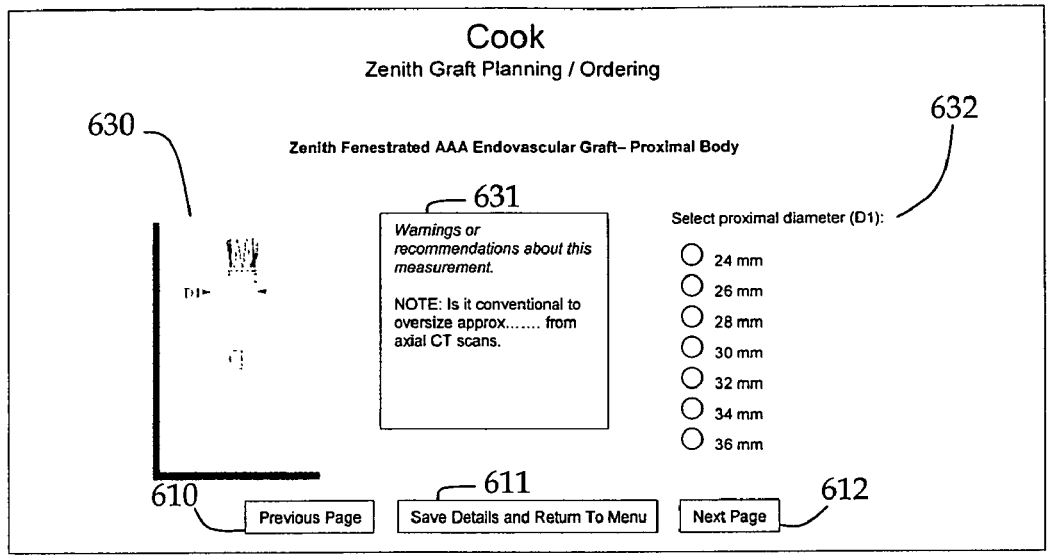
FIG. 8 is a depiction of the proximal diameter D1 selection screen.

Referring now to FIG. 8, the next stage in the graft design process is specifying the proximal diameter D1 of the graft. The physician is presented with a list of proximal diameters 632 ranging from 24 mm to 36 mm in 2 mm increments. An example image 630 depicting the physical location of the proximal diameter being specified again provides the physician with a visual cue of the parameter that is being specified. Information panel 631 includes any warnings or recommendations regarding measuring or estimating the proximal diameter D1. Once again the physician may choose to save the current design at this stage 611, return to the previous screen to make a modification 610 if desired or advance to the next page 612 of the graft design.

Figure 9:
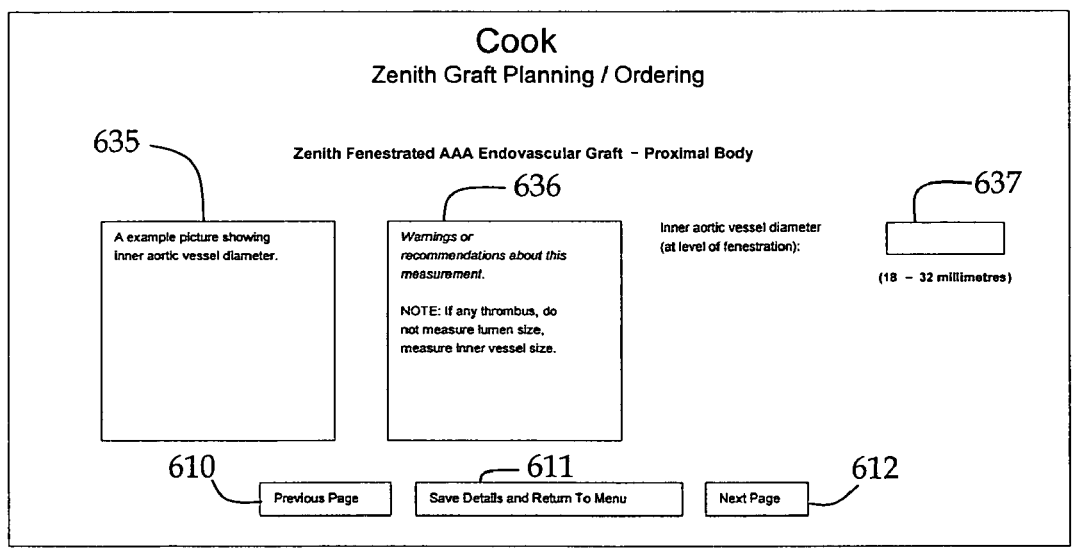
FIG. 9 is a depiction of the inner aortic vessel diameter specification screen.

Referring now to FIG. 9, in the next screen or web page the inner aortic diameter is specified at the location of the fenestration. Example image 635 depicts the location where the diameter of the inner aortic vessel is assessed and information panel 636 indicates any warnings or recommendations to be taken into account when determining the inner aortic vessel diameter. The required diameter is entered at entry field location 637 and verified to be within the range of 18 to 32 mm.

Referring now to FIG. 10, there is shown the screen for specifying the type and location of any fenestrations that are required for the graft. Up to three fenestrations 640, 650, 660 may be specified. Considering now "Fenestration 1" 640, a type selection drop down list 641 allows the physician to choose either a scallop, large or small fenestration. In this example, a scallop fenestration is chosen. The next step is to enter the clock position of the fenestration from drop down list 642 with reference to clock position diagram 646. The clock position can be selected in increments of 15 minutes ranging from 1.00 to 12.75 (in decimal hours). In this example a value of 01:00 has been entered, corresponding to a predominately anterior positioned scallop fenestration located just to the left of the full anterior position. The height of the scallop is then entered 643 and verified according to the type of fenestration selected.

For "Fenestration 2" 650 a large fenestration is chosen 651 at a location of 01:00 652. Associated input fields are dynamically displayed and updated depending on the type of fenestration. For a large fenestration, the diameter 653 must be specified and also the distance addition, design and ordering system 100 confirms the order by email 260 and displays order confirmation screen 300 to allow physician 210 to check the details of the graft. After this the physician may logout 275. In the event that physician 210 does not supply a purchase order 235B, the graft design is saved and an order status of PENDING is set 245 by design and ordering system 100. The status of the order is then further saved 245A in central database 130. Design and ordering system 100 then emails physician 210 details of the pending order 250 and the physician 210 is then able to complete the order by following the instructions on order completion instructions screen 270. At this stage, physician 210 is able to supply the required purchase order number 280 either by the ordering system or alternatively via facsimile.

Figure 3:
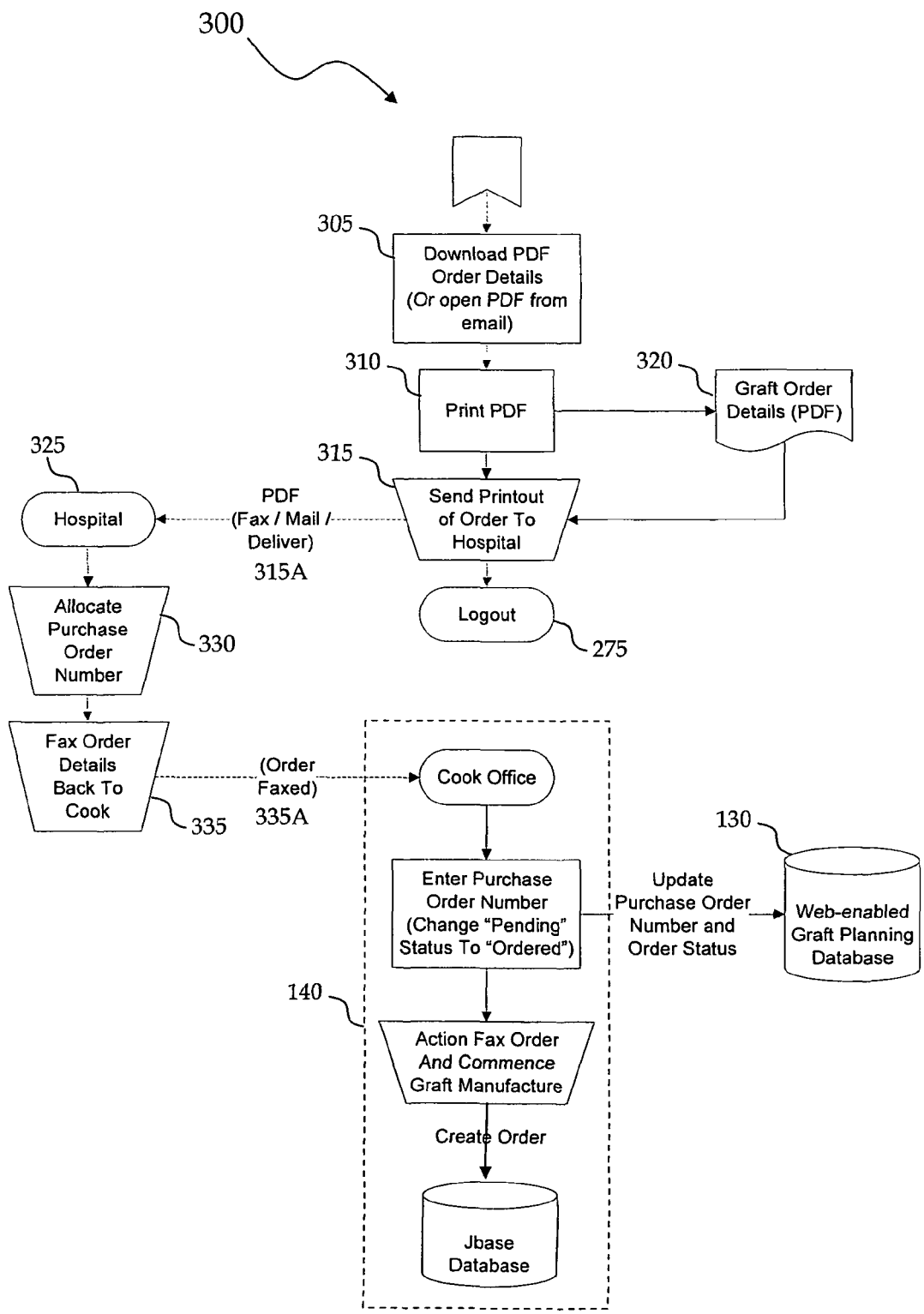
FIG. 3 is a system flowchart depicting the ordering process via facsimile or email once a graft design has been completed.

Referring now to FIG. 3, there is shown a flowchart of the order completion process 300 where a purchase order number is faxed to manufacturing coordination 140. Physician 210 either downloads 305 order details from design and ordering system 100 or alternatively prints 310 out order details which were emailed 210 as part of the ordering process. Physician 210 sends these details 315 to hospital 325 either via fax, mail or delivery 31 5A which then allocates a purchase order number 330 and sends the order details 335 to manufacturing coordination 140 by fax 335A.

Once manufacturing coordination 140 has received the order details, including an allocated purchase number from hospital 325, the order status is updated to ORDERED by manufacturing coordination 140 entering design and ordering system 100 and updating the order details to include the purchase number. These order details, including the order status, are then further saved in central database 130.

Figure 4:
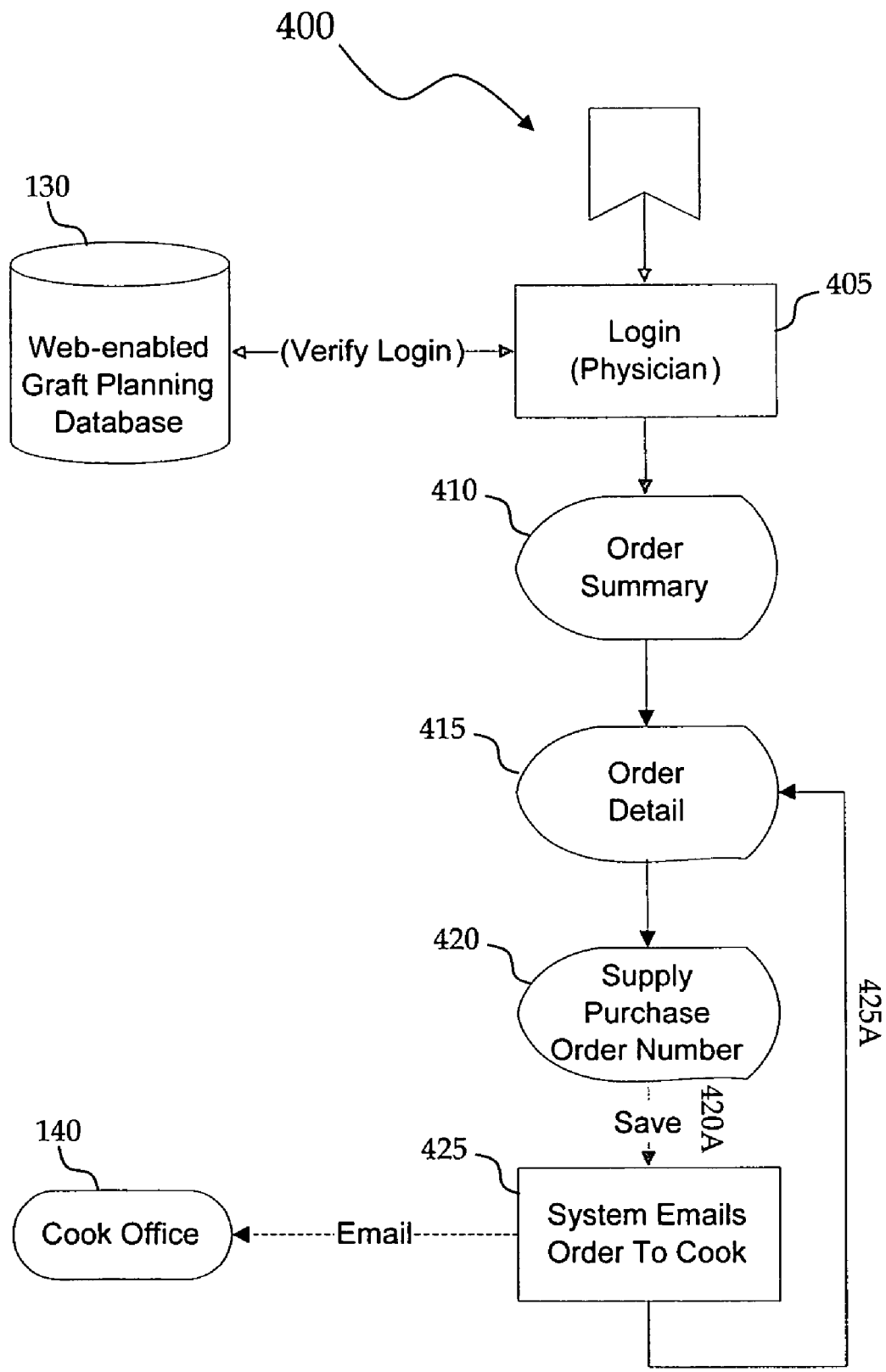
FIG. 4 is a system flowchart depicting the ordering process using the web based interface once a graft design has been completed.

Referring now to FIG. 4, there is shown a flowchart of the order completion process 400 where a purchase order number is subsequently entered into design and ordering system 100. Physician 210 once again from the edge 654. The lower boundary of the distance from the edge is set at 10 mm and the upper boundary is calculated according to the formula $$\text{Upper Boundary} = DFB - (\text{fenestration diameter}/2) - 5\text{ mm}$$

where DFB is defined as the distance to fenestration boundary.

At "Fenestration 3" 660, a small type fenestration is selected at drop down list 661 once again at a clock location of 01:00 662. For this type of fenestration the height can be selected from the options of 6 mm or 8 mm 663. The lower boundary of the distance from the edge 664 is set at 15 mm and the upper boundary is calculated according to the formula set out above. If no fenestration is required then a "blank" option may be chosen.

Figure 12:
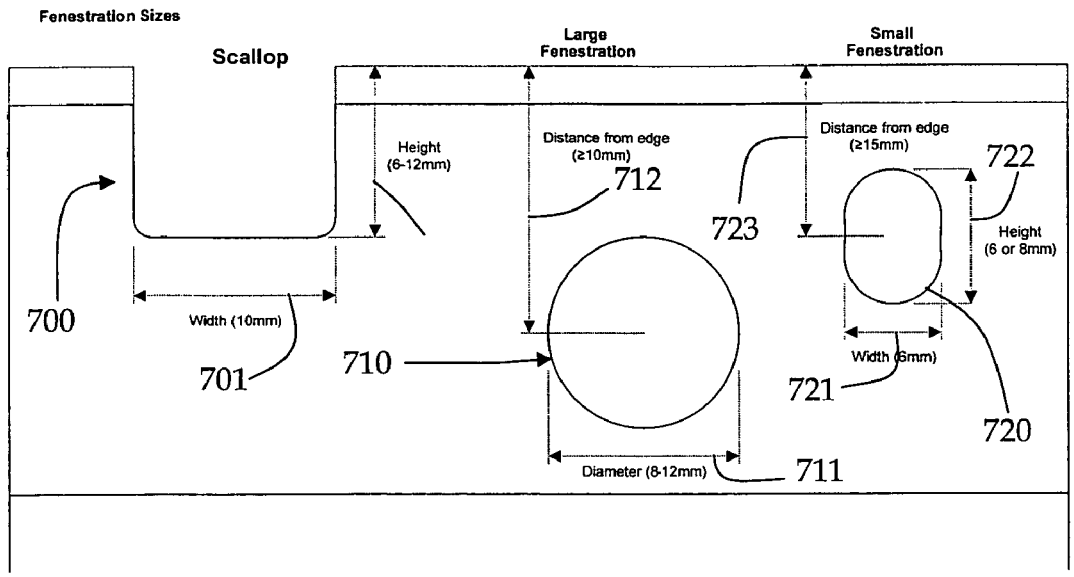
FIG. 12 is an overview of the fenestration shapes and dimensions.
Figure 13:
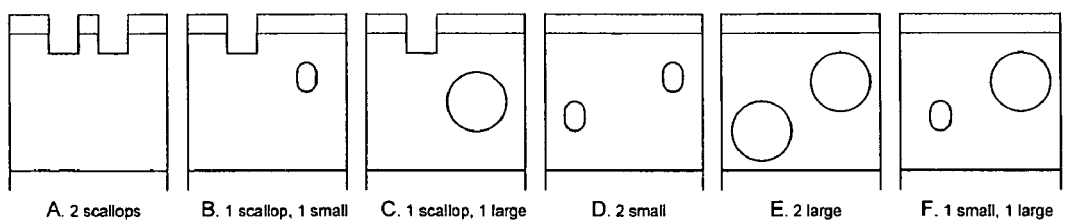
FIG. 13A to 13L depicts the possible fenestration pair combinations for both single and twin stent graft designs.
Figure 13:
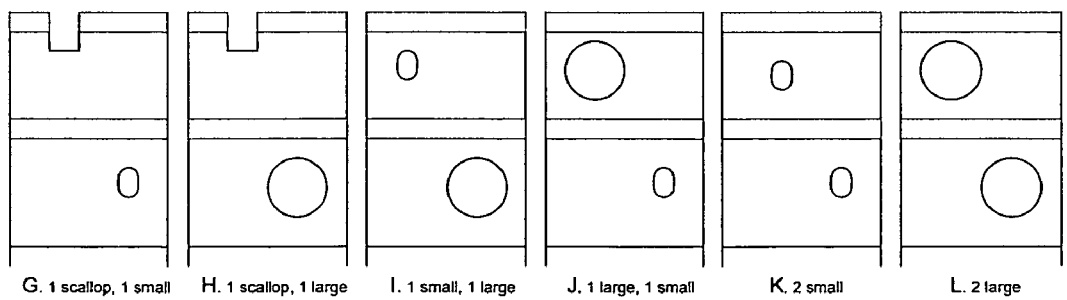

Referring now to FIGS. 11a and 11b, there is shown the positioning and height of stents as dependent on the wire gauge that is used in the proximal fenestrated grafts. These dimensions will be referenced in the validation rules described below. All measurements are in millimetres. FIG. 12 depicts the range of sizes and positioning available for each type of fenestration or scallop which also are input parameters to the validation procedure. Not only do fenestrations and scallops have to be validated individually, pairs of fenestrations and/or scallops are also validated according to the validation scheme set out in FIG. 13 and discussed herein.

These validation rules differ depending on whether the two fenestrations are in the same stent or in located different stents. Note that scallops only occur in the upper stent.

To validate each scallop individually, the following parameters are verified:
  clock position=1.00 to 12.75 inclusive;
  height=6 to 12 mm inclusive; and
  note that scallops are always located in the upper stent.

To validate each large fenestration individually, the following parameters are verified:
  clock position=1.00 to 12.75 inclusive;
  diameter=8 to 12 mm inclusive; and
  check that DFE ranges from 10 mm to (DFB−(fenestration diameter/2)−5 mm)
  inclusive, where DFE is the distance from the edge.

In the case of a graft having two stents, it is first necessary to determine which stent the fenestration is in by calculating whether DFE is less than DFB for the equivalent one stent graft. If this is true, then the fenestration is flagged as being in the upper stent otherwise the fenestration is flagged as being in the lower stent. Clearly, a large fenestration is either in one stent or the other as it cannot overlap the gap between the stents. Where the large fenestration is flagged as being in the upper stent, then a check is performed to determine whether $$DFE+(\text{fenestration diameter}/2)>DFB$$

for the equivalent one stent graft. If this is the case then the fenestration extends into the gap between the stents and an error condition will be flagged.

If alternatively the large fenestration is flagged as being in the lower stent then a check is performed to determine whether $$DFE-(\text{fenestration diameter}/2)-3<DFB$$

for an equivalent one stent graft. If this is the case then the fenestration extends into the gap between the stents and an error condition will be flagged.

To validate each small fenestration individually, the following parameters are verified:
  clock position=1.00 to 12.75 inclusive
  height=6 or 8 mm; and
  DFE=ranges from 15 to (DFB−(fenestration height/2)−5 mm) inclusive.

Similarly, for a graft having 2 stents, the stent the fenestration is located in determined by calculating whether DFE<DFB for an equivalent one stent graft. If this is the case then the fenestration is flagged as being in the upper stent otherwise it is flagged it as being in the lower stent.

Figure 14:
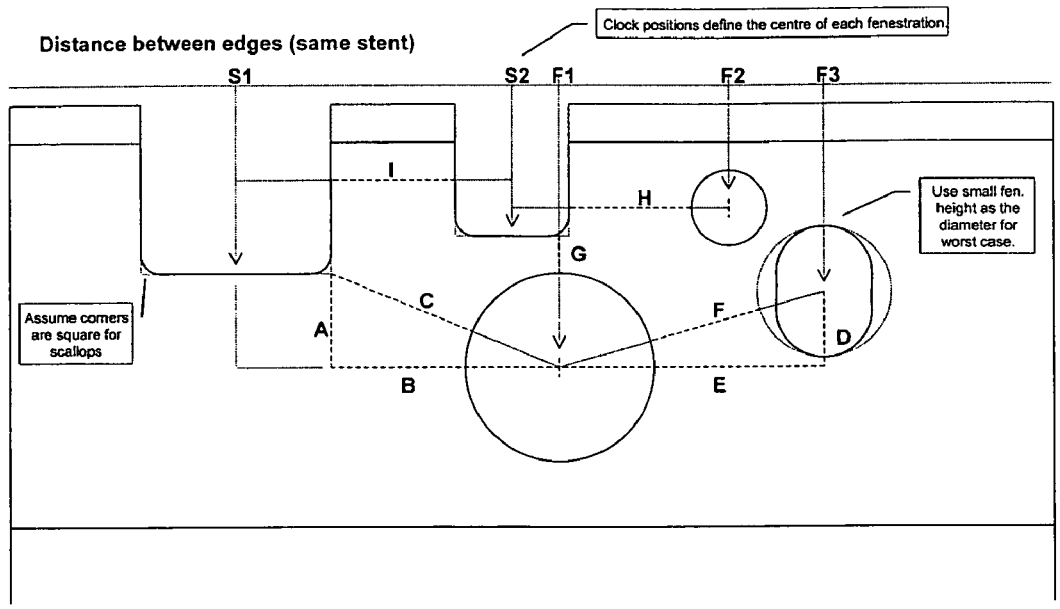
FIG. 14 is a detailed schematic view of the physical dimensions and their locations for fenestration pairs located in the same stent.
Figure 15:
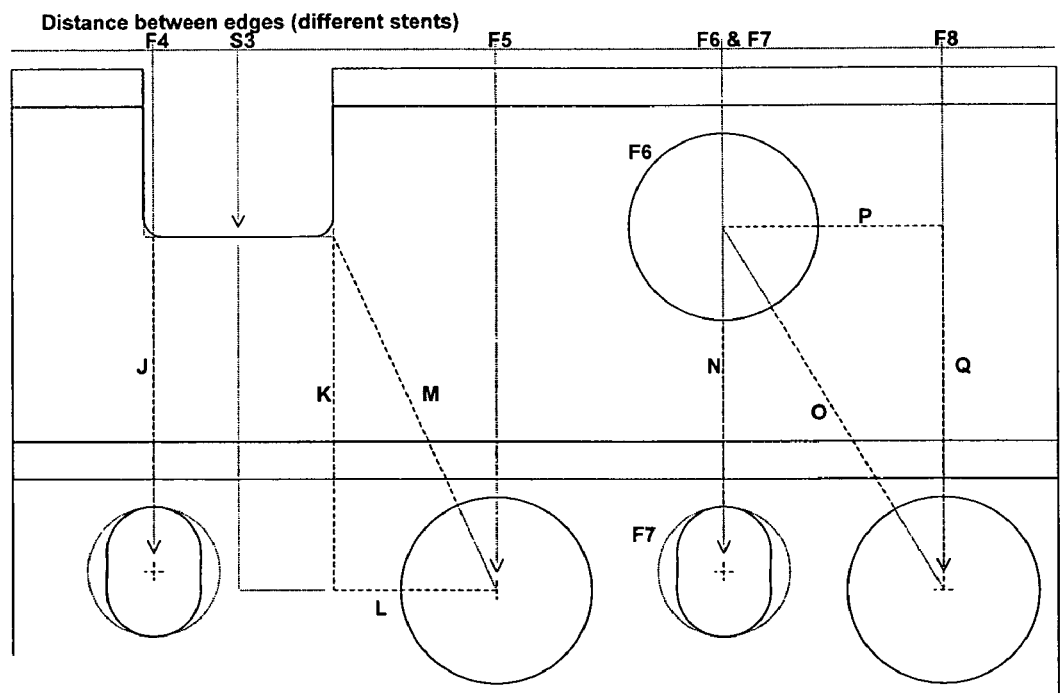
FIG. 15 is a detailed schematic view of the physical dimensions and their locations for fenestration pairs where individual fenestrations are located in separate stents.

Referring now to FIGS. 14 and 15, these depict the relevant fenestration dimensions for validating the distance between edges of fenestrations and/or scallops for grafts having either one stent (FIG. 14) or two stents (FIG. 15). For these validation calculations, scallops are assumed to have square corners and furthermore it is assumed that given that small fenestrations are always 6 mm wide but either 6 or 8 mm high, then small fenestrations will be always represented by a 8 mm diameter circle when the height is selected to be 8 mm thereby catering for the worst case.

The first step to validate pairs of fenestrations and or scallops is to assess their relative separation with respect to each other and their placement on the stent. Each scallops or fenestration is assigned a number 1, 2 or 3 (e.g. S1, F2, F3) after their details have been entered. Validations are then performed for each pair applying the following rules:
  if only one scallop or fenestration is entered then no comparison validations are required;
  if 2 scallops or fenestrations are entered then validate 1 and 2; and
  if 3 scallops or fenestrations are entered, first validate 1 and 2, then 1 and 3 and then 2 and 3.

The following reference formulae and constants are then be used when validating pairs of fenestrations or scallops:
  Pi=3.14
  Aortic vessel expansion value=1 mm
  Distance per hour (mm/hr)=(inner aortic vessel diameter+ aortic vessel expansion)*Pi/12 hrs
  Horizontal separation (between centres) (hrs)=

$$hrs=abs(\text{clock posn.1}-\text{clock posn.2})$$

If hrs>6 then, hrs=(12−hrs)

(Note: This formula provides the minimum separation hours from either the clockwise or anti-clockwise separation hours.)
  Horizontal distance (between centres) (mm)=Distance per hour*Horizontal separation (hrs)
  Minimum length of graft material required between the edges of fenestrations and scallops=5 mm. (Note: this may not necessarily be a horizontal measurement.)
  Horizontal distance (between edges) (mm)=Horiz dist− (fen/scallop1 width/2)−(fen/scallop2 width/2).
  For 24-32 mm diameter grafts, 18 gauge wire stents are used:
    Wire diameter ($D_w$)=0.4572 mm
    Inner radius of the stent point ($R_p$)=0.5 mm
  For 34-36 mm diameter grafts, 20 gauge wire stents are used:
    Wire diameter ($D_w$)=0.508 mm
    Inner radius of the stent point ($R_p$)=0.5 mm
  Minimum horizontal distance (required for stent placement) between edges of small fenestrations and scallops in the same stent:
    $W_s=(2*(RP*2))+(3*DW)$
  $W_s$ is 3.37 mm for 18 gauge and 3.53 mm for 20 gauge
  Minimum horizontal distance (required for stent placement) between edges of two small fenestrations, or two small scallops, in the same stent:

$$W_s=(3*(RP*2))+(4*DW)$$

$W_s$ is 4.82 mm for 18 gauge and 5.032 mm for 20 gauge.
  Vertical distance (between edges large fen/scallop) (mm)= (large fen. DFE−(large fen. diameter/2)−scallop height.
  Vertical distance (between edges small fen/scallop) (mm)= (small fen. DFE−(small fen. height/2)−scallop height.
    Vertical separation (between centres) (mm)= DFE(fen.1)−DFE (fen.2).
  Distance between edges at nearest point (non-scallop) (mm)=
  ($\sqrt{((\text{vertical separation}^2)+(\text{horizontal separation}^2))})-(\text{diameter fen.1}/2)-(\text{diameter fen.2}/2)$.
  (Note: For small fenestrations, the height is used as the diameter to provide a "worst case" answer.)

Referring now to FIG. 13A and FIG. 14, the validation rules for two scallops in the same stent include:
  Check the horizontal distance between edges require
Referring now to FIG. 13A and FIG. 14, the validation rules for two scallops in the same stent include:
  Check the horizontal distance between edges required for stent placement. This value should be ≧the minimum of 4.82 mm or 5.032 mm depending on the gauge.
  Check the distance between the edges to allow for minimum graft material. In this example, this is always the same as the horizontal distance between the edges (see distance I between S1 and S2 in FIG. 14). This value should be ≧the minimum length of graft material (i.e. 5 mm).

Referring now to FIG. 13B and FIG. 14 the validation rules for one scallop and one small fenestration in the same stent include:
  Check the horizontal distance between edges required for stent placement: This value should be ≧the minimum of 3.37 mm or 3.53 mm depending on the gauge.
  Check if the distance from edge (DFE) for the small fenestration is less than or equal to the height of the scallop.
This should always be false as the maximum height of a scallop is 12 mm and the distance from the edge for small fenestrations is always ≧ or equal to 15 mm.
  If the small fenestration distance from edge (DFE) is ≦the scallop height (which will not happen with the current parameters), then the distance between the edges to allow for minimum graft material will be the same as the horizontal distance between edges. This value should be ≧the minimum length of graft material (i.e. 5 mm).
  If the small fenestration distance from edge (DFE) is >the scallop height (which will always be the case with the current parameters), and the small fenestration cannot be "below" the scallop due to the minimum separation required for stent placement, then the distance between the edges to allow for minimum graft material is be calculated by finding the distance at the nearest point (see distance C between S1 and F1 in FIG. 14). The horizontal separation value B will be the horizontal distance–(scallop width/2). The vertical separation A is calculated as normal and the final distance between the edges is calculated as $(\sqrt{((\text{vertical separation}^2)+(\text{horizontal separation}^2))})-(\text{diameter small fenestration}/2)$. As discussed previously, the height of the small fenestration is set as the diameter to cater for the worst case scenario (e.g. fenestration F3 in FIG. 14). This value should be ≧the minimum length of graft material (i.e. 5 mm).

Referring now to FIG. 13C and FIG. 14 the validation rules for one scallop and one large fenestration in the same stent include:
  As stents can cross the lumen of large fenestrations, the horizontal distance between the edges required for stent placement does not need to be calculated.
  As the distance from the edge (DFE) for large fenestrations is ≧10 mm and the maximum height of a scallop is 12 mm, it is possible for the horizontal position of the centre of the large fenestration to be above the base of the scallop (see for example S2 and F2 in FIG. 14). Therefore if the distance from the edge (DFE) is ≦the height of the scallop, then the distance between the edges to allow for minimum graft material is the same as the horizontal distance. This value should be ≧the minimum length of graft material (i.e. 5 mm).
  If the distance from the edge (DFE) is >the height of the scallop, then the fenestration centre may be horizontally positioned within the edges of the scallop (see for example S2 and F1 in FIG. 14). In this case, the distance between the edges to allow for minimum graft material is calculated as the vertical separation G. This value should be ≧the minimum length of graft material (i.e. 5 mm).
  If the distance from the edge (DFE) is >the height of the scallop and the centre of the fenestration is outside the edges of the scallop (see example S1 and F1 in the diagrams above), then the distance between the edges to allow for minimum graft material is calculated as the distance between edges at nearest point C. This value should be ≧the minimum length of graft material (i.e. 5 mm).

Referring now to FIG. 13D and FIG. 14 the validation rules for two small fenestrations in the same stent include:
  Check the horizontal distance between edges required for stent placement. This value should be ≧the minimum of 4.82 mm or 5.032 mm depending on the gauge.
  If the distance from the edge (DFE) is the same for both small fenestrations, then the distance between the edges to allow for minimum graft material is the same as the horizontal distance between the edges. This value should be ≧the minimum length of graft material (i.e. 5 mm).
  If the clock positions for both small fenestrations are the same, the distance between the edges to allow for minimum graft material is calculated as the vertical distance. This value should be ≧the minimum length of graft material (i.e. 5 mm).
  If the distance from the edge (DFE) for both small fenestrations is different, then the distance between the edges to allow for minimum graft material is calculated as the distance between edges at nearest point. This value should be ≧the minimum length of graft material (i.e. 5 mm).

Referring now to FIG. 13E and FIG. 14 the validation rules for two large fenestrations in the same stent include:
  As stents can cross the lumen of large fenestrations, the horizontal distance between the edges required for stent placement does not need to be calculated.
  If the distance from the edge (DFE) is the same for both large fenestrations, then the distance between the edges to allow for minimum graft material is the same as the horizontal distance between the edges. This value should be ≧the minimum length of graft material (i.e. 5 mm).
  Whilst highly unlikely, the clock positions for both large fenestrations may be the same. In this case, the distance between the edges to allow for minimum graft material is calculated as the vertical distance. This value should be ≧the minimum length of graft material (i.e. 5 mm).
  If the distance from the edge (DFE) for both large fenestrations is different and the clock positions are different, then the distance between the edges to allow for minimum graft material is calculated as the distance between edges at nearest point. This value should be ≧the minimum length of graft material (i.e. 5 mm).

Referring now to FIG. 13F and FIG. 14 the validation rules for one small and one large fenestration in the same stent include:
  As stents can cross the lumen of large fenestrations, the horizontal distance between the edges required for stent placement does not need to be calculated.
  If the distance from the edge (DFE) is the same for both fenestrations, then the distance between the edges to allow for minimum graft material is the same as the horizontal distance between the edges. This value should be ≧the minimum length of graft material (i.e. 5 mm).
  If the clock positions are the same then the distance between the edges to allow for minimum graft material is calculated as the vertical distance. This value should be ≧the minimum length of graft material (i.e. 5 mm).
  If the distance from the edge (DFE) for both fenestrations is different and the clock positions are different, then the distance between the edges to allow for minimum graft material is calculated as the distance between edges at nearest point. (Note: use the height of the small fenestrations as the diameter to cater for the worst case scenario). This value should be ≧the minimum length of graft material (i.e. 5 mm).

Referring now to FIGS. 13G, 13H and FIG. 15 the validation rules for one scallop, and one small or one large fenestration in different stents include:

Small and large fenestrations are treated the same in these scenarios, as the height of the small fenestration is set as the diameter, to cater for the worst case. As the scallop will always be in the upper stent, the small/large fenestration will be in the lower stent. Two possible situations can occur:

The fenestration centre could be horizontally positioned within the edges of the scallop (see example S3 and F4 in FIG. 15). In this case, the distance between the edges to allow for minimum graft material is calculated as the vertical separation J. This value should be ≧the minimum length of graft material (i.e. 5 mm).

If the centre of the fenestration is outside the edges of the scallop (see example S3 and F5 in FIG. 15), then the distance between the edges to allow for minimum graft material is calculated as the distance between edges at nearest point M. This value should be ≧the minimum length of graft material (i.e. 5 mm).

Referring now to FIGS. 13I, 13J, 13K, 13L and FIG. 15 the validation rules for one small and one large, two small or two large fenestrations in different stents include:

Small and large fenestrations are treated the same in these scenarios, as we use the height of the small fenestration as the diameter, to cater for the worst case. Two possible situations can occur:

Both fenestration centres could be horizontally positioned on the same clock position. (see example F6 and F7 in the diagrams above). In this case, the distance between the edges to allow for minimum graft material is calculated as the vertical separation N. This value should be ≧the minimum length of graft material (5 mm).

If the fenestrations are on different clock positions (see example F6 and F8 in the diagrams above), then the distance between the edges to allow for minimum graft material is calculated as the distance between edges at nearest point O. This value should be ≧the minimum length of graft material (5 mm).

As would be apparent to those skilled in the art, the fenestration design and validation procedure described herein will help to ensure that the resulting graft will meet the patient's requirements by giving the physician the ability to specify the graft fenestration design in detail. As various parameters of the fenestrations are validated during the design process this ensures that a physician will be notified of a potentially incorrect fenestration configuration whilst completing the design. This allows the physician to correct any error in the midst of this design process without having to wait until the graft design is completed thus resulting in a more efficient design process.

Figure 16:
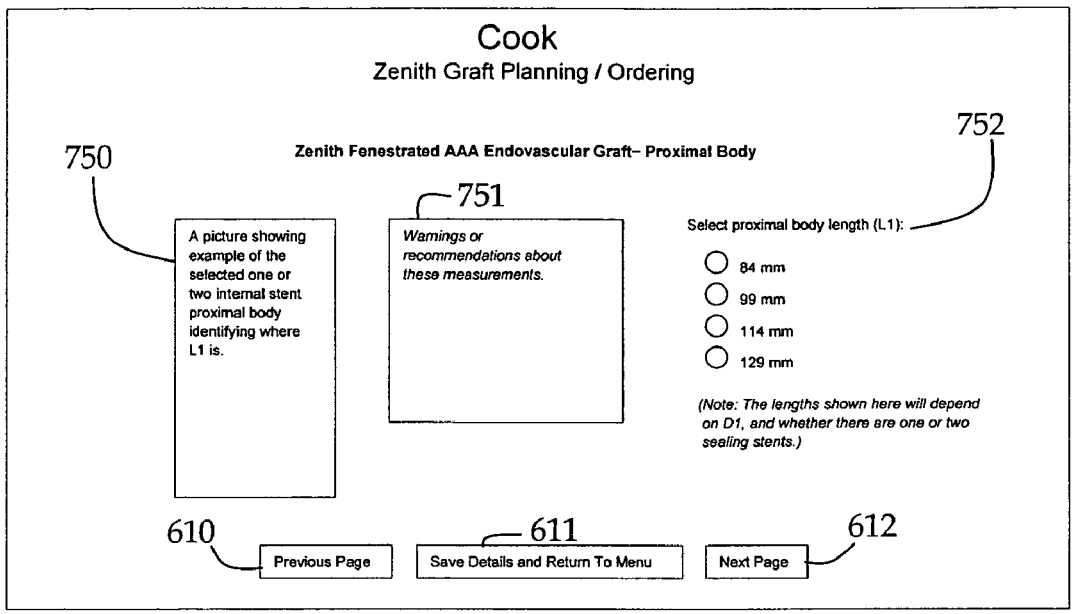
FIG. 16 is a depiction of the proximal body length L1 selection screen.

Referring now to FIG. 16, the next stage in the graft design process once the once the design and validation of any fenestrations have been completed is specifying the proximal body length L1 of the graft. The physician is presented with a screen including a list of proximal body lengths 752 ranging from 84 mm to 129 mm in 15 mm increments. An example image 750 depicting the proximal body indicates the location of L1 provides the physician with a visual cue of the parameter that is being specified. Information panel 751 includes any warnings or recommendations that may be relevant to specifying this parameter. The physician may at this stage choose to save the current design 611 or to move to either the previous page 610 or to the next page 612.

Figure 17:
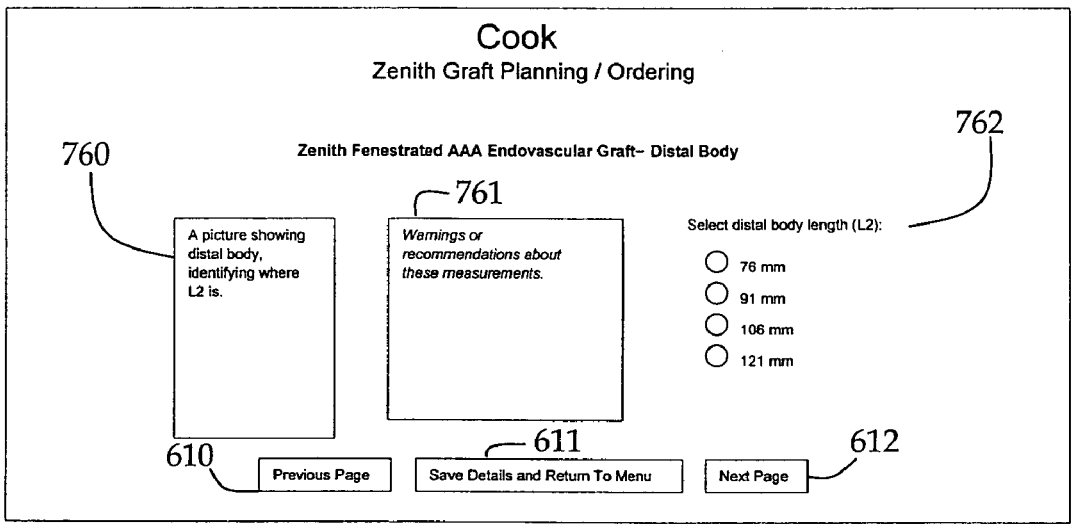
FIG. 17 is a depiction of the distal body length L2 selection screen.

Referring now to FIG. 17, the next stage in the graft design process is specifying the distal body length L2 of the graft. The physician is presented with a screen including a list of distal body lengths 762 ranging from 76 mm to 121 mm in 15 mm increments. An example image 760 depicting the distal body indicates the location of L2 provides the physician with a visual cue of the parameter that is being specified. Information panel 761 includes any warnings or recommendations that may be relevant to specifying this parameter.

Figure 18:
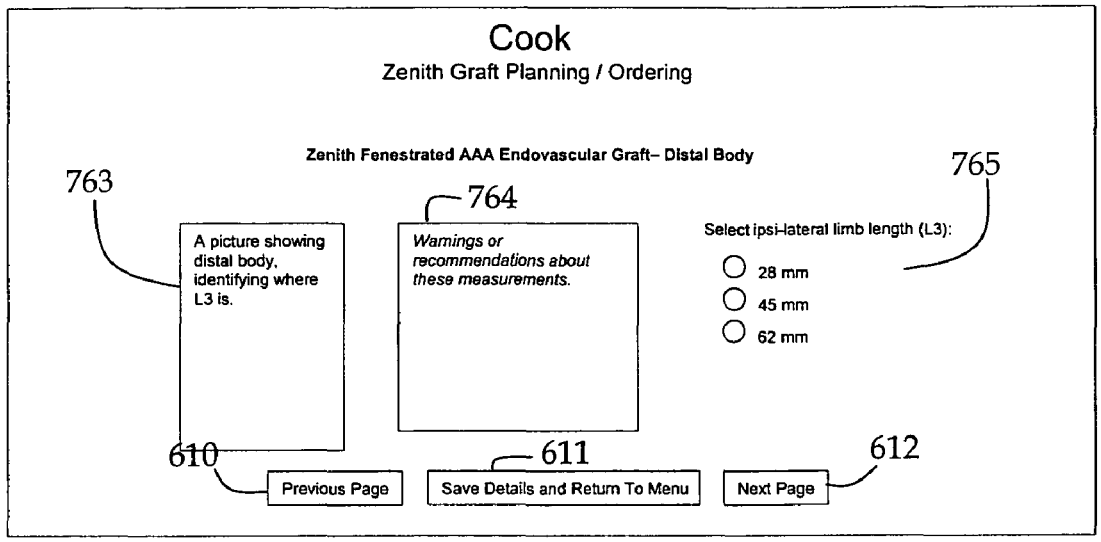
FIG. 18 is a depiction of the ipsi-lateral limb length L3 selection screen.

Referring now to FIG. 18, the following stage in the graft design process is specifying the ipsi-lateral limb length L3 of the graft. The physician is presented with a screen including a list of ipsi-lateral limb lengths 765 ranging from 28 mm to 62 mm in 17 mm increments. An example image 763 depicting the distal body and indicating the location of L3 provides the physician with a visual cue of the parameter that is being specified. Information panel 764 includes any warnings or recommendations that may be relevant to specifying this parameter.

Figure 19:
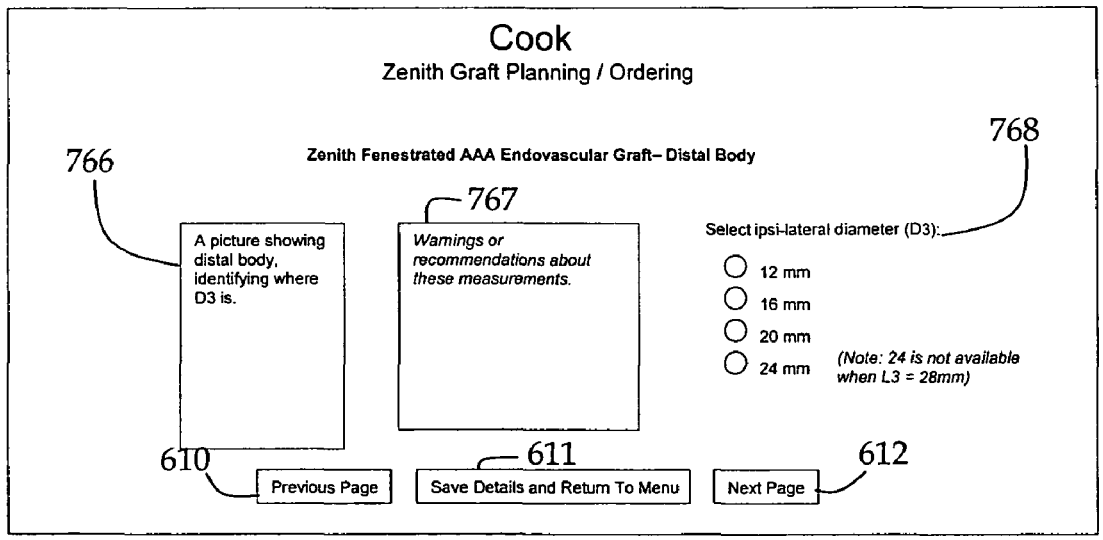
FIG. 19 is a depiction of the ipsi-lateral diameter D3 selection screen.

Referring now to FIG. 19, the next stage in the graft design process is specifying the ipsi-lateral diameter D3 of the graft. The physician is presented with a screen including a list of ipsi-lateral limb diameters 768 ranging from 12 mm to 24 mm in 4 mm increments for selection. An example image 766 depicting the distal body and indicating the location of D3 provides the physician with a visual cue of the parameter that is being specified. Information panel 767 includes any warnings or recommendations that may be relevant to specifying this parameter.

Figure 20:
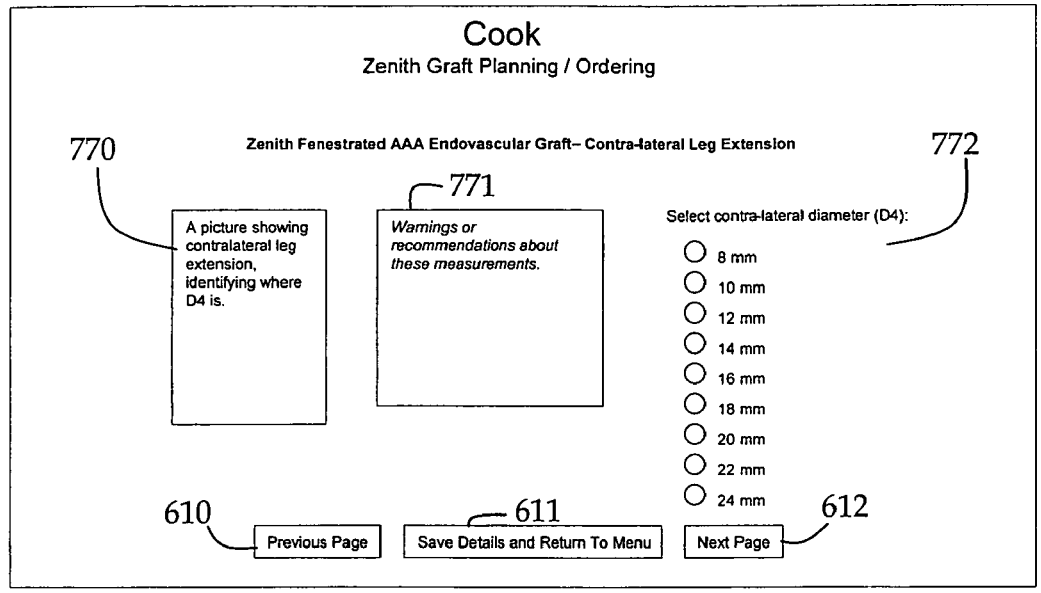
FIG. 20 is a depiction of the contra-lateral diameter D4 selection screen.

Referring now to FIG. 20, the next stage in the graft design process is specifying the contra-lateral diameter D4 of the graft. The physician is presented with a screen including a list of contra-lateral limb diameters 772 ranging from 8 mm to 24 mm in 2 mm increments for selection. An example image 770 depicting the contra-lateral leg extension and indicating the location of D4 provides the physician with a visual cue of the parameter that is being specified. Information panel 771 includes any warnings or recommendations that may be relevant to specifying this parameter.

Figure 21:
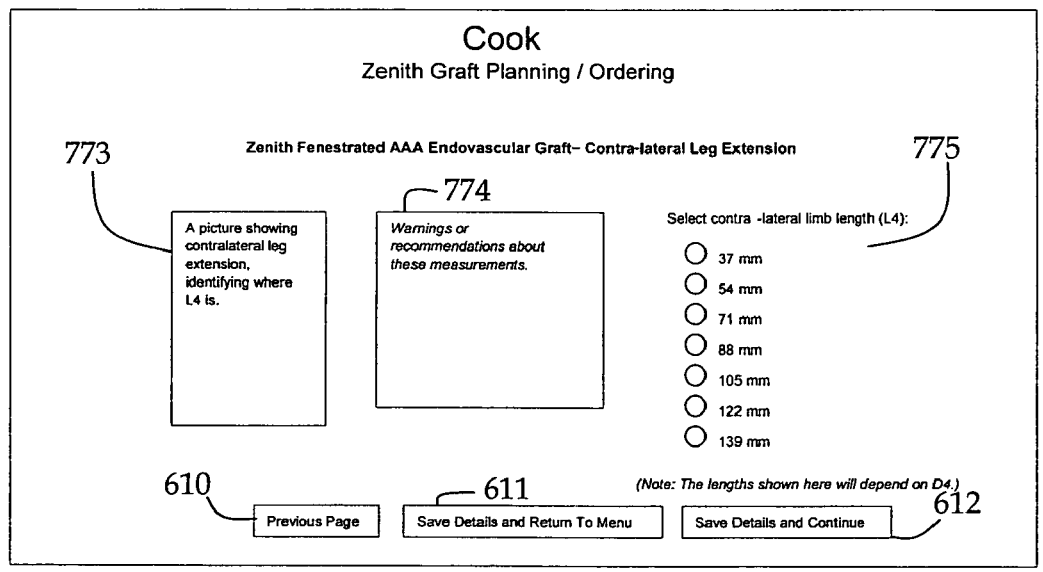
FIG. 21 is a depiction of the contra-lateral limb length L4 selection screen.

Referring now to FIG. 21, the final stage in the graft design process is specifying the contra-lateral limb length L4 of the graft. The physician is presented with a screen including a list of contra-lateral limb lengths 775 ranging from 37 mm to 139 mm in 17 mm increments for selection. An example image 773 depicting the contra-lateral leg extension and indicating the location of L4 provides the physician with a visual cue of the parameter that is being specified. Information panel 774 includes any warnings or recommendations that may be relevant to specifying this parameter.

Figure 22:
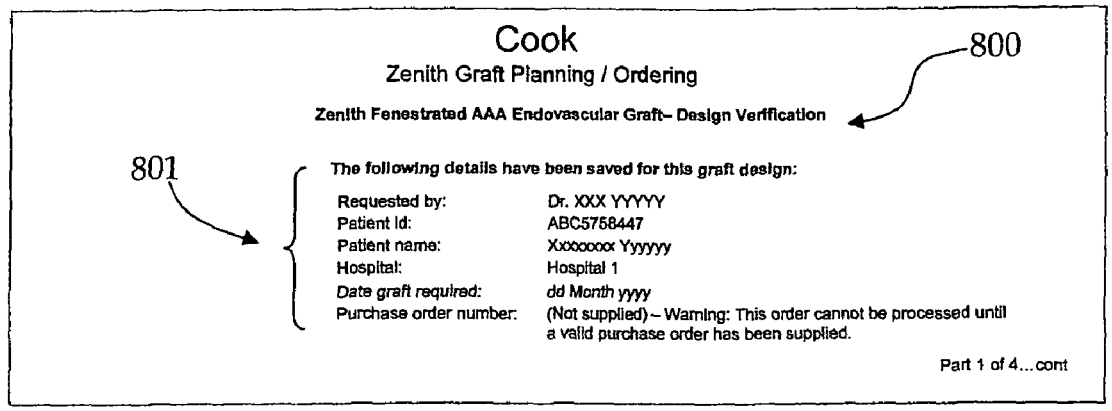
FIG. 22 is a depiction of the first design verification screen indicating identification details for the completed graft design.
Figure 23:
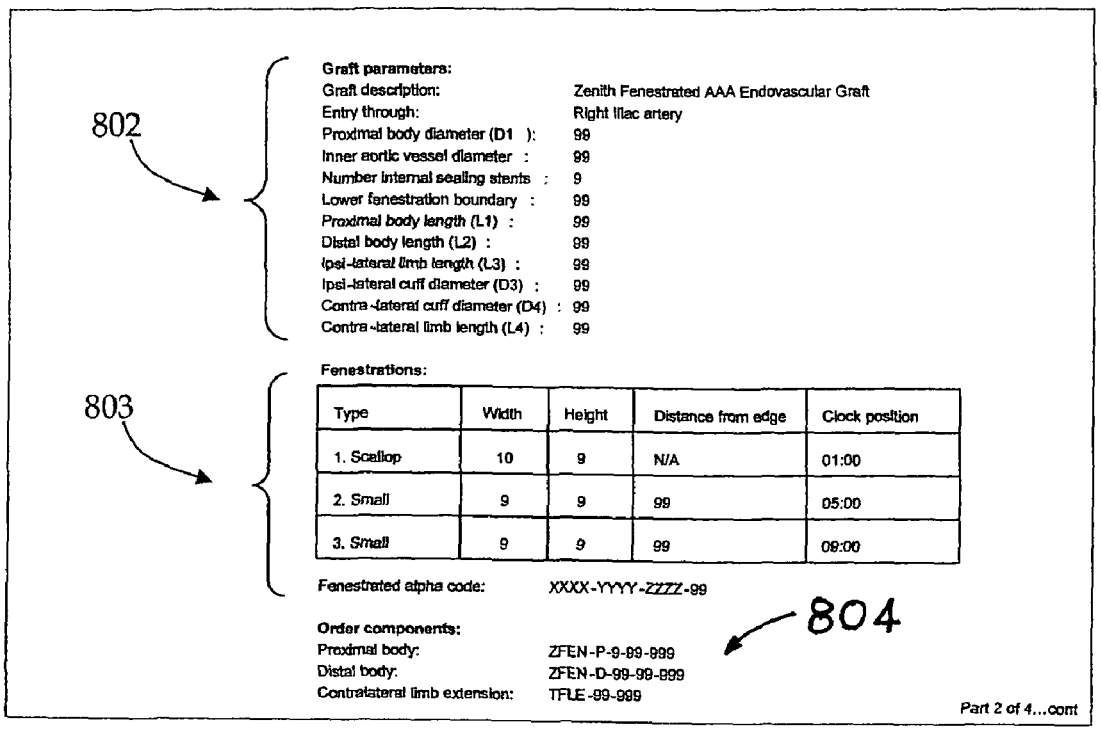
FIG. 23 is a depiction of the second design verification screen listing graft and fenestration details for the completed graft design.

Once the graft design has been completed, the next stage is to review the relevant details of the design including patient and ordering information as well as the configuration of the graft. Referring now to FIGS. 22 to 26, the physician is presented with verification details of the completed graft design. As shown in FIG. 22, the first verification screen displays the graft design type 800 and identification information 801 detailing both relevant patient and physician details and a field for the purchase order number. The second verification screen includes a listing of the relevant graft parameter details 802 and fenestration details 803 setting out the details of each fenestration that is included in the graft. Also listed are alpha-numeric ordering codes 804 for each of the components of the graft design.

Figure 24:
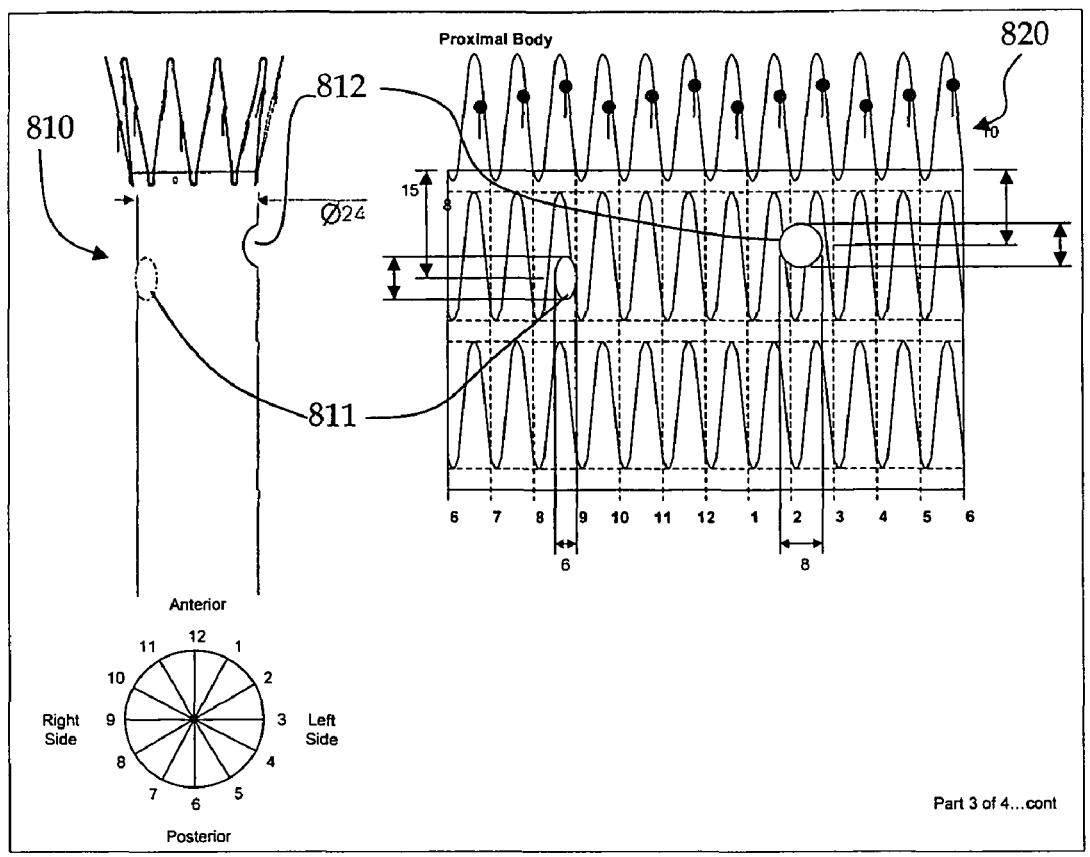
FIG. 24 is a depiction of the third design verification screen depicting two dimensional representations of the proximal body of the completed graft design.
Figure 25:
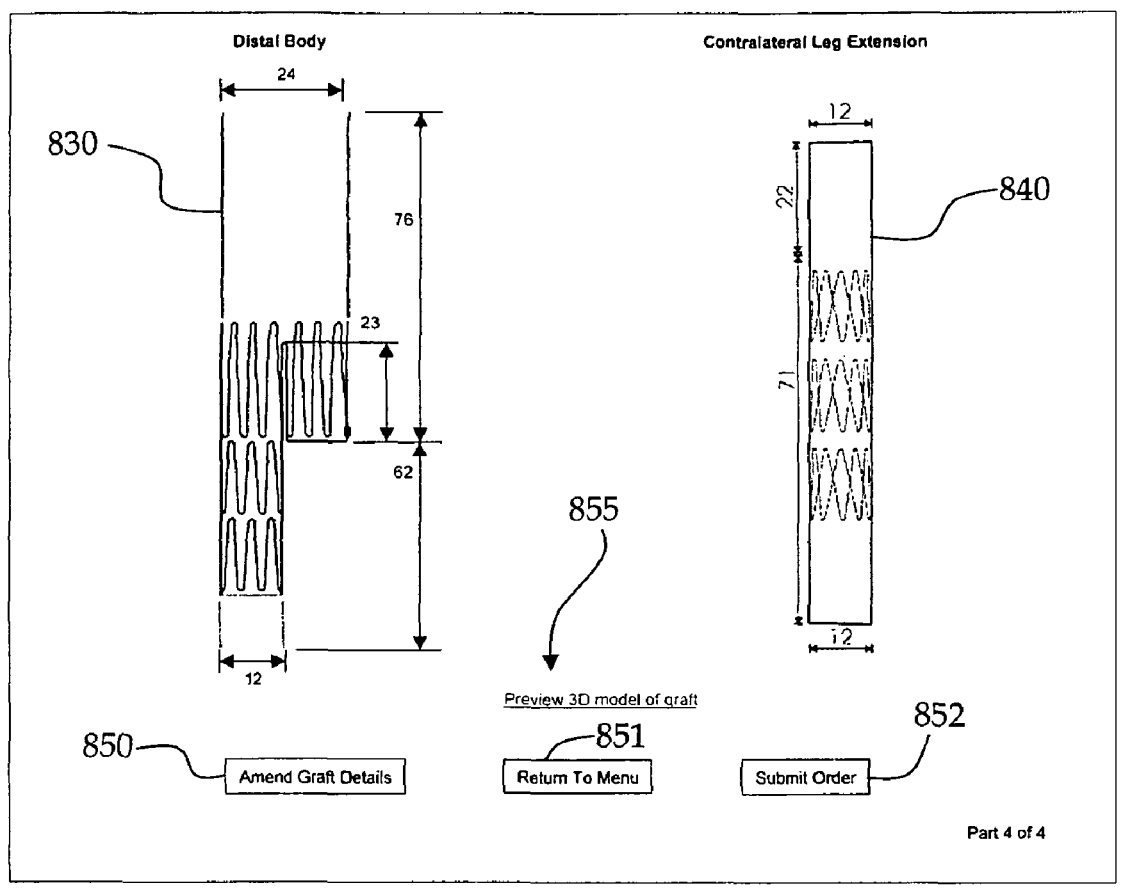
FIG. 25 is a depiction of the fourth design verification screen depicting two dimensional representations of the distal body and the contralateral leg extension of the completed graft design.
Figure 26:
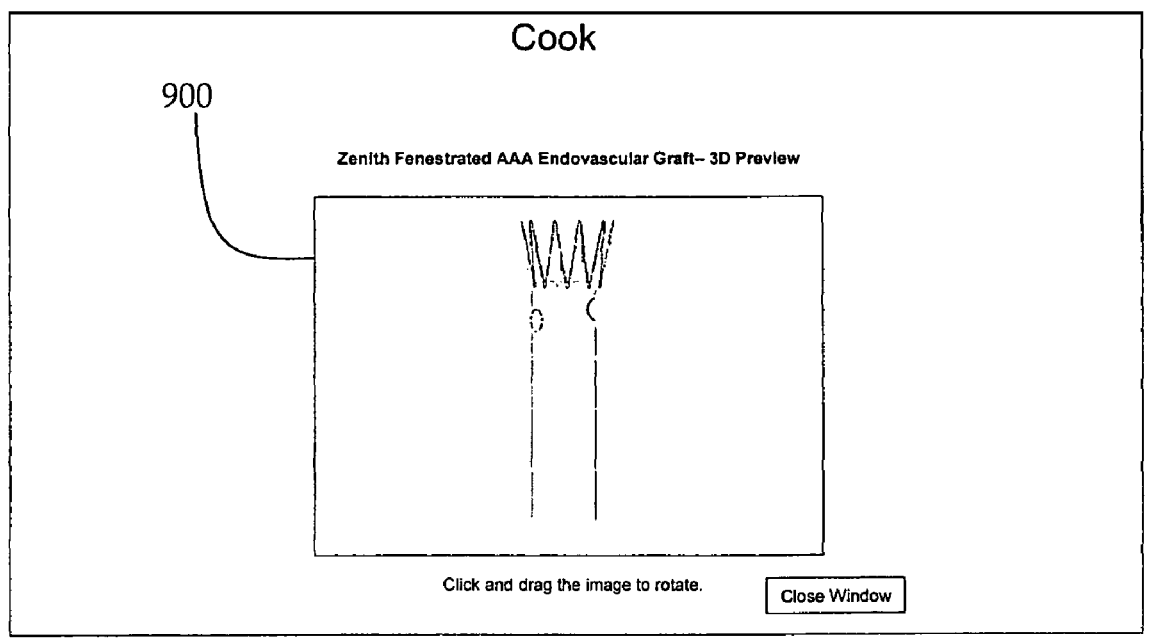
FIG. 26 is a screen shot of the 3-dimensional verification screen according to a preferred embodiment of the present invention.

Referring now to FIG. 24, there are shown 2D representations of the proximal body of the completed graft. First view 810 depicts a side view of proximal body indicating in this case the position of fenestrations 811, 812. Second view 820 depicts a flattened rolled out view of the proximal body indicating the location of the fenestrations shown in side view 810 with overlayed reference markings showing their physical dimensions and exact positioning. In FIG. 25, similar side views of both the distal body 830 and the contra-lateral leg extension 840 are shown which also include overlayed reference markings which show the values of relevant physical dimensions. The physician is also able to select a 3D preview mode 855 of the final graft design which is shown in FIG. 26. In this screen, a orientable 3D model of the final graft design 900 is shown. The physician can them simply by using the mouse or keyboard either zoom in, rotate or re-position the completed graft design to better view the graft configuration.

When viewing the 3D preview 900 of the completed graft design the physician may also be presented with the option to overlay the values of the relevant physical parameters similar to that shown for the 2D representations (as best seen in FIGS. 24 and 25). Alternatively, 3D anatomical details of the graft site sourced from patient measurements may be overlayed onto the completed graft design to also verify that the completed graft configuration matches the requirements of the patient. On completing review of the 3D representation of the graft design the physician returns to the previous screen and at this stage may choose to amend the design 850, return to the top level menu 851 or if the physician is satisfied with the completed design then submit an order.

A brief consideration of the above described embodiment will indicate that the invention provides an improved system for designing and ordering a stent graft which addresses many of the deficiencies of prior art systems including the ability to design and order using a centralised design tool which does not require updating the software individual users when new versions are released. In this preferred embodiment, related to the design of grafts, the invention provides for the ability to include sophisticated design features in the medical implant such as fenestrations. Another advantageous feature is the ability to view an orientable 3D image of the medical implant as part of the design verification and review process.

Throughout the specification the terms "graft" and "stent graft" have been used interchangeably to refer to surgically implanted grafts which may be of unitary or multipart construction for the treatment of vascular and other related diseases.

Although a preferred embodiment of the method and system of the present invention has been described in the foregoing detailed description, it will be understood that the invention is not limited to the embodiment disclosed, but is capable of numerous rearrangements, modifications and substitutions without departing from the scope of the invention as set forth and defined by the following claims.

What is claimed is:

1. A system for designing and ordering a stent graft, the system comprising:
   a user interface for designing and ordering the stent graft, the user interface comprising;
   a selection portion for selecting a stent graft design; and
   a design portion for entering a plurality of design parameters related to the stent graft design;
   a centralised data processor remote from and in communication with the user interface for processing and storing information entered into the user interface;
   the centralised data processor comprising a data store arrangement to store data relating to design parameters of a stent graft; the data store also containing a 3-dimensional view of a patient stent graft site sourced from patient measurements for comparison with a completed stent graft design; and
   a processing arrangement to process required design parameters related to the stent graft design to produce the completed stent graft design,
   the user interface further comprising;
   a verification portion to verify details of a completed stent graft design, the verification portion including a design verification screen to display a view of the completed stent graft design;
   the view being a 3-dimensional view of the completed stent graft design; and the 3-dimensional view being reorientable to inspect the completed stent graft design;
   an overlay portion to overlay the completed stent graft design in the 3-dimensional view with the 3-dimensional view of a patient stent graft site from the data store; and
      an ordering portion to enable a user to order the completed stent graft design.

2. The system for designing and ordering a stent graft as claimed in claim 1, wherein the 3-dimensional view is zoomable to inspect the completed stent graft design.

3. The system for designing and ordering a stent graft as claimed in claim 1, wherein the selection portion includes a selection of a stent graft having at least one fenestration.

4. The system for designing and ordering a stent graft as claimed in claim 3, where the design portion includes at least one screen, the at least one screen adapted to capture fenestration design information related to the at least one fenestration.

5. The system for designing and ordering a stent graft as claimed in claim 4, wherein the fenestration design information includes the fenestration type.

6. The system for designing and ordering a stent graft as claimed in claim 5, wherein the fenestration type is selectable from a large, small or scallop type fenestration.

7. The system for designing and ordering a stent graft as claimed in claim 4, wherein the fenestration design information includes the location of the at least one fenestration.

8. The system for designing and ordering a stent graft as claimed in claim 7, wherein the location of the at least one fenestration includes a distance from an edge of the stent graft.

9. The system for designing and ordering a stent graft as claimed in claim 7, wherein the location of the least one fenestration is selectable as a clock position.

10. The system for designing and ordering a stent graft as claimed in claim 4, wherein the fenestration design information includes the size of the at least one fenestration.

11. The system for designing and ordering a stent graft as claimed in claim 4, wherein the system includes a validation capability to validate the fenestration design information related to the at least one fenestration.

12. The system for designing and ordering a stent graft as claimed in claim 11, wherein the validation capability includes validating a size, location and type of the at least one fenestration.

13. The system for designing and ordering a stent graft as claimed in claim 12, wherein the validation capability, includes in the case of more than one fenestration, validating the combination of fenestrations for the stent graft design.

14. A system for designing and ordering a stent graft as claimed in claim 1, wherein the system includes the storage and recall of an incomplete stent graft design.

15. A method for the design and ordering of a stent graft, the method including the steps:

(a) designing or specifying a value for a physical parameter of a stent graft design employing a user interface;
(b) validating the value against predetermined criteria related to the physical parameter employing a centralized data processor remote from and in communication with the user interface;
(c) storing the value in a data store arrangement of the centralized data processor remote from the user interface;
(d) repeating steps (a)-(c) until a completed stent graft design has been designed;
(e) verifying the completed stent graft design on completion of the design of the stent graft by displaying on the user interface a 3-dimensional view of the completed stent graft design;
(f) reorienting the 3-dimensional view of the completed stent graft design to inspect the completed stent graft design;
(g) overlaying the 3-dimenstional view of the completed stent graft design over a 3-dimensional view of a patient stent graft site sourced from patient measurements and stored in the data store arrangement to verify that the completed stent graft design matches the requirements of the patient stent site; and
(h) ordering the stent graft via the user interface.

* * * * *